(12) United States Patent
Hirayama et al.

(10) Patent No.: US 6,383,520 B1
(45) Date of Patent: May 7, 2002

(54) FINE POWDER OF L-α-AMINOADIPIC ACID DERIVATIVE, ORAL SOLID PREPARATIONS CONTAINING THE SAME, AND METHOD FOR TREATMENT OF BULK POWDERS

(75) Inventors: Tomoaki Hirayama; Hiroshi Murata, both of Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/720,307

(22) PCT Filed: Jun. 25, 1999

(86) PCT No.: PCT/JP99/03408

§ 371 Date: Dec. 26, 2000

§ 102(e) Date: Dec. 26, 2000

(87) PCT Pub. No.: WO00/00492

PCT Pub. Date: Jan. 6, 2000

(30) Foreign Application Priority Data

Jun. 26, 1998 (JP) .................................... 10-180724

(51) Int. Cl.[7] .............................. A61K 9/14; A61K 9/20; A61K 9/48

(52) U.S. Cl. ...................... 424/489; 424/451; 424/464; 514/951

(58) Field of Search ................................ 424/451, 452, 424/456, 464, 489

(56) References Cited

U.S. PATENT DOCUMENTS 5,728,692 A * 3/1998 Ohi et al. ................ 514/224.2
5,958,928 A * 9/1999 Mihara ........................ 514/258

FOREIGN PATENT DOCUMENTS

JP 519711 A * 1/1976
JP 6271552 A * 2/1987
JP 6239863 A * 8/1994

* cited by examiner

*Primary Examiner*—James M. Spear
(74) *Attorney, Agent, or Firm*—Browdy and Neimark

(57) ABSTRACT

A crystalline bulk powder of N-(1-((2,4-diamino-6-pteridinyl)methyl)-3,4-dihydro-2H-1,4-benzothiazine-7-carbonyl)L-α-aminoadipic acid is treated by using an impact grinding method or a jet mill grinding method to give a finely ground powder. Solid oral preparations containing the thus obtained finely ground powder as the active ingredient can quickly release the active ingredient and high content uniformity can be ensured without adversely affecting the stability.

10 Claims, 2 Drawing Sheets

FINE POWDER OF L-α-AMINOADIPIC ACID DERIVATIVE, ORAL SOLID PREPARATIONS CONTAINING THE SAME, AND METHOD FOR TREATMENT OF BULK POWDERS

This application is a 371 of PCT/JP99/03408 filed Jun. 25, 1999.

TECHNICAL FIELD

This invention relates to a finely ground powder of N-(1-((2,4-diamino-6-pteridinyl)methyl)-3,4-dihydro-2H-1,4-benzothiazine-7-carbonyl)L-α-aminoadipic acid (hereinafter also referred to as MX-68), a method for treating a bulk MX-68 powder, solid oral preparations containing this finely ground powder as the active ingredient, and a method for producing the same.

BACKGROUND ART

Bulk powder of MX-68, studies on which are in progress as a novel antirheumatic, can be separated depending on difference in crystallization solvents into an amorphous fine powder and a crystalline bulk powder involving coarse particles, having a wide particle size distribution and showing slight orientation. The amorphous bulk powder of MX-68, which is obtained mainly from organic solvent solutions, shows an extremely high dissolution speed and a high degree of mixing with additives because of being a fine powder. However, it suffers from a disadvantage of having poor stability. On the other hand, the crystalline bulk powder of MX-68, which is obtained mainly from aqueous solutions, is superior in stability to the amorphous bulk powder. However, there has been discovered a problem that this crystalline bulk powder cannot ensure high content uniformity in preparations due to the low solubility and non-uniform particle size thereof. Accordingly, it has been required to provide a means of solving the problems of the solubility and content uniformity while sustaining the high stability of the bulk MX-68 powder. As a means of improving the solubility of the bulk powder and the content uniformity of preparations, attempts have been made to enlarge the surface area of the bulk powder by reducing the particle diameter so as to elevate the dissolution speed. Thus, there have been employed mechanical grinding methods by taking advantage of friction between the bulk powder and a pulverizer such as a ball mill or a hammer mill. It is also known that the dissolution speed can be elevated by making the crystalline bulk powder amorphous. In the case of the crystalline bulk powder of MX-68, however, the stability is lowered with a decrease in the crystallinity. Therefore, it has been required to develop a grinding method whereby the crystalline bulk powder can be finely ground while sustaining its crystallinity.

DISCLOSURE OF THE INVENTION

The present inventors have conducted intensive studies to solve the above-described problems. As a result, they have successfully found that a finely ground powder having an average particle diameter of 5 to 25 μm and sustaining the crystallinity can be obtained by finely grinding a crystalline bulk powder of MX-68 by an impact grinding method or a jet mill grinding method and preparations having improved dissolution properties and content uniformity can be obtained by using the finely ground powder thus obtained. The present invention has been completed based on these findings.

Accordingly, the present invention provides a finely ground powder of MX-68 which has an average particle diameter of 5 to 25 μm and sustains its crystallinity even after grinding.

The present invention further provides solid oral preparations containing as the active ingredient a finely ground powder of MX-68 which has an average particle diameter of 5 to 25 μm and sustains its crystallinity even after grinding.

The present invention further provides a method for treating a bulk powder of MX-68 which comprises grinding a crystalline bulk powder of MX-68 to give a finely ground powder of MX-68 having an average particle diameter of 5 to 25 μm and sustaining its crystallinity even after grinding.

The present invention furthermore provides a method for producing solid oral preparations containing as the active ingredient a finely ground powder of MX-68 which involves the step of grinding a crystalline bulk powder of MX-68 by using an impact grinding method or a jet mill grinding method.

According to the present invention, a crystalline bulk powder of MX-68 is treated by using an impact grinding method or a jet mill grinding method so that solid oral preparations showing rapid release of the active ingredient and ensuring high content uniformity can be obtained without adversely affecting the stability. In the present invention, the crystalline bulk powder of N-(1-((2,4-diamino-6-pteridinyl)methyl)-3,4-dihydro-2H-1,4-benzothiazine-7-carbonyl)L-α-aminoadipic acid can be obtained in accordance with the method as will be described in Example 1 hereinafter (i.e., the method described in Japanese Laid-Open Patent Publication No. 6-239863(A)) which comprises adjusting an alkaline aqueous solution of MX-68 to its isoelectric point and crystallizing. Alternatively, this crystalline bulk powder can be obtained by adjusting an acidic aqueous solution of MX-68 to its isoelectric point followed by crystallization. Moreover, crystalline powders obtained by other methods are also usable as the crystalline bulk powder of MX-68 in the present invention.

BEST MODE FOR CARRYING OUT THE INVENTION

Figure 1:
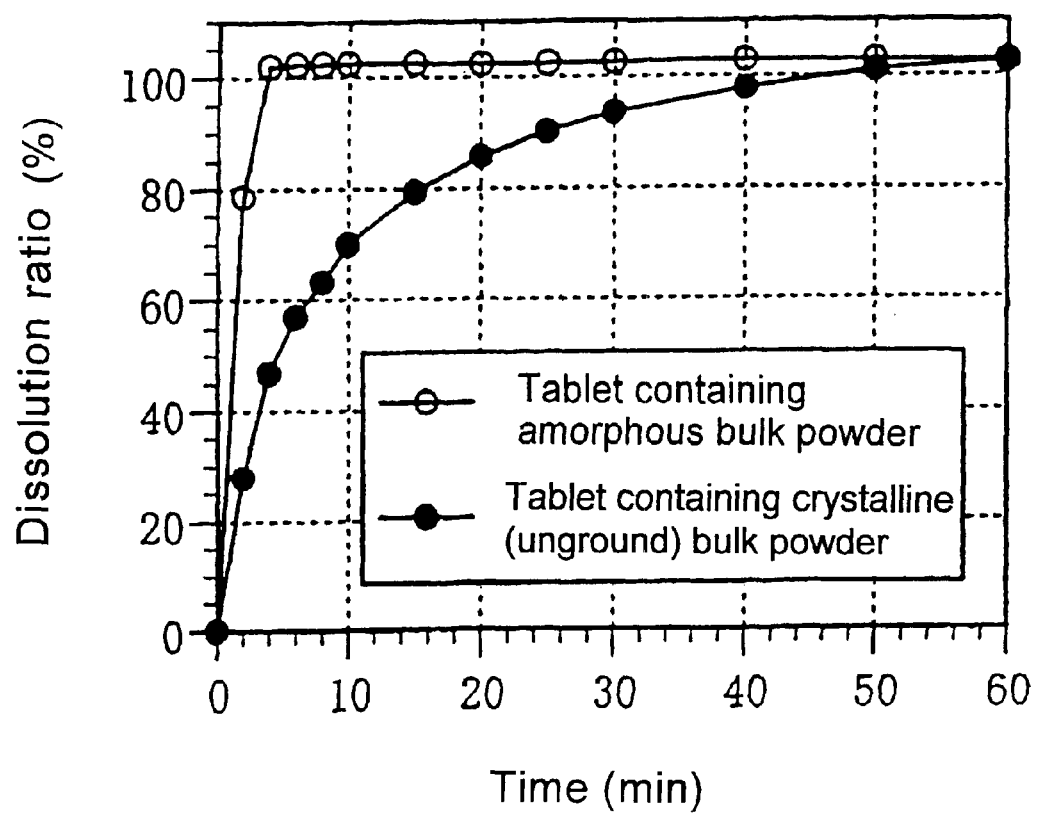
FIG. 1 is a graph which shows the dissolution curves of tablets containing the crystalline bulk powder of MX-68 and tablets containing an amorphous bulk powder.
Figure 2:
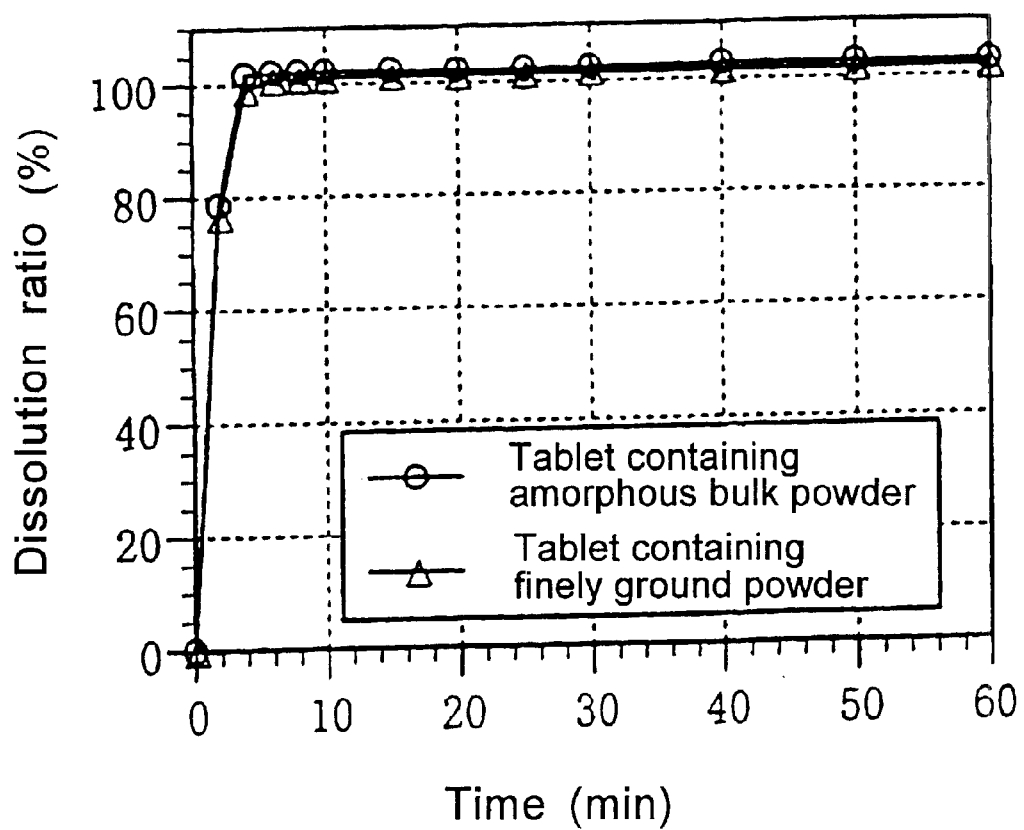
FIG. 2 is a graph which shows the dissolution curves of tablets containing the preparation according to the present invention and tablets containing an amorphous bulk powder of MX-68.

The average particle diameter of the finely ground powder of MX-68 in the present invention can be measured by using, for example, a dry particle size distribution measurement apparatus (AEROSIZER mach 2, manufactured by AMHERST PROCESS INSTRUMENTS, INC) as will be described in Example 1 hereinafter. The finely ground powder of MX-68 according to the present invention has an average particle diameter of from 5 to 25 μm. When the average particle diameter is less than 5 μm, the finely ground powder is liable to be charged with static electricity and thus there arises a high possibility of dusting and adhesion. When the average particle diameter exceeds 25 μm, on the other hand, it is feared that the solubility and/or content uniformity of MX-68 are adversely affected. It is preferable that the average particle diameter ranges from 8 to 15 μm, still preferably from 9 to 11 μm.

The term "grinding treatment" as used herein means a procedure whereby a ground powder with a smaller size can be obtained with the use of the impact at the collision between the bulk powder and an impact unit (for example, an impact plate, a pin, a edge, a hammer, a blade or a cutter), and/or collisions among bulk powder particles. Thus, it is clearly distinguishable from the conventional grinding treatment by taking advantage of the friction between the bulk powder and a grinder. As preferable examples of the grinding treatment, the impact grinding method and the jet mill grinding method may be cited. According to this grinding treatment, the particle size distribution ratio at 5 to 30 μm can be elevated to 80% or more.

The impact grinding method is a grinding method carried out by using high-speed rotational impact grinders which are roughly classified into three types, i.e., rotary disc grinders, screen mills and centrifugal mills depending on the function. Any of these types is appropriately usable in the present invention. A rotary disc grinder is provided with a rotor in the form of a rotary disc having pins and edges thereon. As this rotor rotates at a high speed, these pins and edges collide with the sample which is thus cut, sheared and ground. Examples of the rotary disc grinder include a centrifugal grinder (manufactured by Nippon Seiki Seisakusho), an impact mill (manufactured by K.K. Dalton), etc. In a screen mill, a sample is finely ground via collision with a hammer which rotates at a high speed. Examples of the screen mill include an atomizer (manufactured by Tokyo Atomizer Seizo K.K.), a sample mill (manufactured by Tokyo Atomizer Seizo K.K.), a bantam mill (manufactured by Tokyo Atomizer Seizo K.K.), etc. In a centrifugal mill, particles are carried on a gas stream along the axis and then finely ground by an impact plate rotating at a high speed.

In the jet mill grinding method to be used in the present invention, a jet grinder is used and a sample powder is incorporated into a jet air stream injected at a high speed and high pressure and thus finely ground due to collisions among the particles. As an example of the jet grinder, a micro-labo jet mill (A-O Jet Mill, manufactured by Seishin Kigyo) may be cited.

In the present invention, the impact grinding method and the jet mill grinding method employed in grinding the crystalline bulk powder of MX-68 are based on the characteristic of the bulk MX-68 powder of being relatively easily ground by the impact at the collisions of the powder with pins or hammers rotating at a high speed in a dry system or collisions among the powder particles under a high-speed gas stream.

The finely ground powder of MX-68 sustaining the crystallinity according to the present invention means a finely ground powder of MX-68 which has, both before and after the grinding treatment, parts showing polarization when observed under a polarization microscope, and has an endotherm of from 25 to 50 mJ/mg, preferably from 30 to 50 mJ/g at an endothermic peak appearing, for example, at 185 to 195° C. in the differential scanning calorimetry as will be described Example 2.

The solid oral preparations containing the finely ground powder of MX-68 according to the present invention may be in the form of, for example, powders, fine granules and granules and capsules and tablets produced by using these powders, fine granules and granules. Preferable examples thereof include capsules and tablets produced by using these powders, fine granules and granules.

To produce these preparations, use can be made of publicly known means such as the dry methods and the wet methods. In the production of these preparations, various additives commonly employed in the pharmaceutical field may be blended, so long as the effects of the present invention are not adversely affected thereby. Examples of the additives usable herein include fillers such as lactose, anhydrous lactose, granulated lactose, sucrose, D-mannitol, corn starch, crystalline cellulose, calcium hydrogenphosphate and anhydrous calcium hydrogenphosphate; binders such as hydroxypropylcellulose, hydroxypropylmethylcellulose, gelatinized starch, partially gelatinized starch, corn starch, polyvinylpyrrolidone, methylcellulose and dextrin; disintegrating agents such as hydroxypropylcellulose with low degree of substitution, croscarmellose sodium, carmellose calcium, carmellose sodium, carboxymethylstarch sodium, crospovidone and corn starch; and lubricating agents such as magnesium stearate, calcium stearate, stearic acid, talc and sucrose fatty acid esters.

EXAMPLES

Now, the invention will be described in greater detail by reference to the following examples.

Example 1
Treatment of Finely Grinding Bulk Powder

A crystalline bulk powder of MX-68 obtained by the method described in Japanese Laid-Open Patent Publication No. 6-239863(A)) (manufactured by Chugai Pharmaceutical Co., Ltd.) was manually ground in an agate mortar. Separately, the same bulk powder was ground with a centrifugal grinder (ZM-1, manufactured by Nippon Seiki Seisakusho) by using a screen (pore size: 0.2 mm) at 20,000 rpm. Separately, the same bulk powder was ground with a micro-labo jet mill (A-O Jet Mill, manufactured by Seishin Kigyo). The particle diameter of each finely ground powder of MX-68 thus obtained was measured by using a dry particle size distribution measurement apparatus (AEROSIZER mach 2, manufactured by AMHERST PROCESS INSTRUMENTS, INC) and the average particle diameter was determined. As a result, the average particle diameter could be controlled to 9 to 11 μm by each grinding method (Table 1).

TABLE 1

|  | Average particle diameter (μm) |
| --- | --- |
| Mortar-ground bulk powder | 9.3 |
| Centrifugal-ground bulk powder | 11.4 |
| Jet mill-ground bulk powder | 10.7 |

Example 2
Thermal Analysis

A crystalline bulk powder of MX-68 obtained by the method described in Japanese Laid-Open Patent Publication No. 6-239863(A)) (manufactured by Chugai Pharmaceutical Co., Ltd.) and the finely ground powders of MX-68 obtained by the grinding methods described in Example 1 were thermally analyzed to thereby determine the differential scanning calories (DSC, temperature rise: 5° C./min). Then the endotherm (caused by the endothermic reaction occurring in association with the conversion of crystalline particles in the crystalline bulk powder into the amorphous state) was calculated. As a result, it was found out that the mortar-ground bulk powder showed a decrease in the endotherm, compared with the unground bulk powder, while the centrifugal-ground bulk powder and the jet-mill ground bulk powder showed no change in the endotherm before and after the grinding treatment (Table 1). Namely, it has been clarified that the centrifugal grinding method and the jet mill grinding method do not affect the crystallinity of the crystalline bulk powder.

TABLE 2

|  | Endotherm (mJ/mg) |
| --- | --- |
| Unground bulk powder | 33.5 |
| Mortar-ground bulk powder | 22.3 |
| Centrifugal-ground bulk powder | 32.8 |
| Jet mill-ground bulk powder | 33.2 |

Example 3

Stability

A comparison was made on the storage stability (60° C., 2 weeks) of the crystalline bulk powder of MX-68 obtained by the method described in Japanese Laid-Open Patent Publication No. 6-239863(A)) (manufactured by Chugai Pharmaceutical Co., Ltd.), the mortar-ground bulk powder and the centrifugal-ground bulk powder obtained in Example 1. As a result, it was observed that the mortar-ground bulk powder, which showed a decrease in the crystallinity in Example 2, showed a decrease in stability after the grinding treatment. On the other hand, it was found that the centrifugal-ground bulk powder, which showed no change in the crystallinity before and after the grinding treatment, sustained stability comparable to the unground bulk powder, even after the grinding treatment (Table 3).

TABLE 3

|  | Residual ratio (%) |
| --- | --- |
| Unground bulk powder | 95.3 |
| Motor-ground bulk powder | 90.9 |
| Centrifugal-ground bulk powder | 96.3 |

Example 4

Content Uniformity

The crystalline bulk powder of MX-68 obtained by the method described in Japanese Laid-Open Patent Publication No. 6-239863(A)) (manufactured by Chugai Pharmaceutical Co., Ltd.) and the centrifugal-ground bulk powder obtained in Example 1 were mixed with the additives as listed below in a twin-cylinder mixer at 50 rpm. From each dry mixture powder contained in the mixer, samples were taken up at 6 to 9 points with the passage of time and the MX-68 content in each sample was measured. Thus, the content uniformity was evaluated by comparing the maximum deviations (Table 4). As a result, the maximum deviation of the dry mixture powder containing the unground bulk powder attained 18.9% after mixing for 15 minutes, thus showing considerable dispersion in content uniformity. In contrast thereto, the dry mixture powder containing the centrifugal-ground bulk powder showed a relatively small maximum deviation. Thus, it has been clarified that the content uniformity of the preparation can be improved by the grinding treatment.

[Formula]

| Component | Content (mg) |
| --- | --- |
| MX-68 | 5 |
| granulated lactose | 79.5 |
| corn starch | 15 |
| hydrated silicon dioxide | 0.2 |

-continued

[Formula]

| Component | Content (mg) |
| --- | --- |
| magnesium stearate | 0.5 |
| total | 100. |

TABLE 4

|  | Maximum deviation (%) | | |
| --- | --- | --- | --- |
| Mixing time (min) | 5 | 10 | 15 |
| Unground bulk powder | 6.6 | 6.9 | 18.9 |
| Centrifugal-ground bulk powder | 0.8 | 1.6 | 1.0 |

Example 5

Dissolution Rate

Tablets of the following formula were produced by using the crystalline bulk powder of MX-68 obtained by the method described in Japanese Laid-Open Patent Publication No. 6-239863(A)) (manufactured by Chugai Pharmaceutical Co., Ltd.), an amorphous bulk powder and the centrifugal-ground bulk powder obtained in Example 1. More particularly, MX-68, lactose, crystalline cellulose and croscarmellose sodium were dry-mixed. After adding water, the mixture was kneaded and granulated. Then the granulated matter was dried at 50° C., mixed with magnesium stearate, and press molded to give tablets of 6 mm in diameter. In accordance with the method 2 (paddle method) of the dissolution test as specified in Japanese Pharmacopoeia, these tablets were subjected to the dissolution test using 500 ml of JP official solution 1 at 37° C.

As referential data, Table 5 shows the results of a comparison of pharmacokinetic parameters obtained by orally administering the unground bulk powder and the amorphous bulk powder to dogs (1 mg/kg) and measuring the MX-68 concentration in the blood. Thus, it was clearly observed that the amorphous bulk MX-68 powder showed a higher absorbability. The results of the dissolution test as shown in FIG. 1 also indicate that the tablets containing the unground bulk powder showed a lower dissolution rate than the tablets containing the amorphous bulk powder. Thus, it can be concluded that the unground crystalline bulk powder shows a lower solution speed and a lower bioavailability than the amorphous bulk powder. Next, the dissolution test data of the tablets containing the amorphous bulk powder were compared with the data of the tablets containing the centrifugal-ground bulk powder. As a result, the dissolution rate of the tablets containing the centrifugal-ground crystalline bulk powder of MX-68 showed a remarkably elevated dissolution rate and presented an dissolution profile almost comparable to that of the tablets containing the amorphous bulk powder. These results indicate that the bioavailability would be also improved by finely grinding the crystalline bulk powder of MX-68.

[Formula]

| Component | Content (mg) |
| --- | --- |
| MX-68 | 5 |
| lactose | 65.5 |

-continued

| Component | [Formula] Content (mg) |
|---|---|
| crystalline cellulose | 20 |
| croscarmellose sodium | 5 |
| hydroxypropylcellulose | 4 |
| magnesium stearate | 0.5 |
| total | 100. |

TABLE 5

| | $C_{max}$ (mg/mL) | $T_{max}$ (h) | $AUC_{0 \to 24}$ (ng h/mL) |
|---|---|---|---|
| Unground bulk powder | 462 ± 78 | 1.1 ± 0.3 | 1597 ± 603 |
| Amorphous bulk powder | 650 ± 38 | 0.9 ± 0.1 | 1894 ± 81 |

INDUSTRIAL APPLICABILITY

As described above, preparations showing a remarkably elevated dissolution rate and an improved content uniformity without adversely affecting the stability can be obtained by finely grinding a crystalline bulk powder of MX-68 by the impact grinding method or the jet mill grinding method.

What is claimed is:

1. A finely ground powder of N-(1-((2,4-diamino-6-pteridinyl)methyl)-3,4-dihydro-2H-1,4-benzothiazine-7-carbonyl)L-α-aminoadipic acid having an average particle diameter of 5 to 25 μm and sustaining its crystallinity even after the grinding treatment, said finely ground powder having an endotherm of from 25 to 50 mJ/mg at an endothermic peak appearing at 185 to 195° C. in a differential scanning calorimetry, having, both before and after the grinding treatment, parts showing polarization when observed under a polarization microscope, and showing approximate equivalent endotherm reading compared to an unground bulk powder.

2. A solid oral preparation which contains as the active ingredient a finely ground powder of N-(1-((2,4-diamino-6-pteridinyl)methyl)-3,4-dihydro-2H-1,4-benzothiazine-7-carbonyl)L-α-aminoadipic acid having an average particle diameter of 5 to 25 μm and sustaining its crystallinity even after the grinding treatment, said finely ground powder having an endotherm of from 25 to 50 mJ/mg at an endothermic peak appearing at 185 to 195° C. in a differential scanning calorimetry, having, both before and after the grinding treatment, parts showing polarization when observed under a polarization microscope, and showing approximate equivalent endotherm reading compared to an unground bulk powder.

3. The solid oral preparation as claimed in claim 2 wherein said grinding treatment is performed by an impact grinding method.

4. The solid oral preparation as claimed in claim 2 wherein said grinding treatment is performed by a jet mill grinding method.

5. The solid oral preparation as claimed in claim 2 wherein said solid oral preparation is in the form of powders, fine granules, granules, capsules or tablets.

6. A method for treating a crystalline bulk powder of N-(1-((2,4-diamino-6-pteridinyl)methyl)-3,4-dihydro-2H-1,4-benzothiazine-7-carbonyl)L-α-aminoadipic acid, characterized in that a crystalline bulk powder of N-(1-((2,4-diamino-6-pteridinyl)methyl)-3,4-dihydro-2H-1,4-benzothiazine-7-carbonyl)L-α-aminoadipic acid is ground to give a finely ground powder of N-(1-((2,4-diamino-6-pteridinyl)methyl)-3,4-dihydro-2H-1,4-benzothiazine-7-carbonyl)L-α-aminoadipic acid having an average particle diameter of 5 to 25 μm and sustaining its crystallinity even after the grinding treatment, said finely ground powder having an endotherm of from 25 to 50 mJ/mg at an endothermic peak appearing at 185 to 195° C. in a differential scanning calorimetry, having, both before and after the grinding treatment, parts showing polarization when observed under a polarization microscope, and showing approximate equivalent endotherm reading compared to an unground bulk powder.

7. The treatment method as claimed in claim 6 wherein said grinding treatment is performed by an impact grinding method.

8. The treatment method as claimed in claim 6 wherein said grinding treatment is performed by a jet mill grinding method.

9. A method for producing a solid oral preparation which contains as the active ingredient a finely ground powder of N-(1-((2,4-diamino-6-pteridinyl)methyl)-3,4-dihydro-2H-1,4-benzothiazine-7-carbonyl)L-α-aminoadipic acid, characterized by involving the step of grinding a crystalline bulk powder of N-(1-((2,4-diamino-6-pteridinyl)methyl)-3,4-dihydro-2H-1,4-benzothiazine-7-carbonyl)L-α-aminoadipic acid by using an impact grinding method or a jet mill grinding method, said finely ground powder having an average particle diameter of 5 to 25 μm, and sustaining its crystallinity even after the grinding treatment, said finely ground powder having an endotherm of from 25 to 50 mJ/mg at an endothermic peak appearing at 185 to 195° C. in a differential scanning calorimetry, having, both before and after the grinding treatment, parts showing polarization when observed under a polarization microscope, and showing approximate equivalent endotherm reading compared to an unground bulk powder.

10. The production method as claimed in claim 9 wherein said solid oral preparation is in the form of powders, fine granules, granules, capsules or tablets.

* * * * *